(12) United States Patent
Imaizumi et al.

(10) Patent No.: US 7,479,990 B2
(45) Date of Patent: Jan. 20, 2009

(54) PROGRAMMABLE IMAGE PROCESSING UNIT WHICH DISPLAYS A TENTATIVE IMAGE DURING PROGRAMMING

(75) Inventors: Katsuichi Imaizumi, Hachioji (JP); Yoshinori Takahashi, Hachioji (JP); Nobuyuki Doguchi, Hino (JP); Takeshi Ozawa, Sagamihara (JP); Sakae Takehana, Sagamihara (JP); Isami Hirao, Hachioji (JP)

(73) Assignee: Olympus Corporation, Tokyo (JP)

( * ) Notice: Subject to any disclaimer, the term of this patent is extended or adjusted under 35 U.S.C. 154(b) by 841 days.

(21) Appl. No.: 10/873,949

(22) Filed: Jun. 22, 2004

(65) Prior Publication Data

US 2004/0263643 A1 Dec. 30, 2004

(30) Foreign Application Priority Data

Jun. 27, 2003 (JP) ............................. 2003-185715

(51) Int. Cl.
*H04N 7/18* (2006.01)
*H04N 9/73* (2006.01)
*H04N 5/222* (2006.01)
*A61B 1/06* (2006.01)
*G06K 9/00* (2006.01)

(52) U.S. Cl. ................... 348/223.1; 348/68; 348/370; 382/133; 382/167

(58) Field of Classification Search .............. 348/65, 348/68, 69, 70, 76, 223.1, 224.1, 225.1, 370; 348/655; 382/133, 134
See application file for complete search history.

(56) References Cited

U.S. PATENT DOCUMENTS

| | | | |
|---|---|---|---|
| 5,408,263 A | 4/1995 | Kikuchi et al. | |
| 5,504,525 A * | 4/1996 | Suzuki | 348/223.1 |
| 5,627,583 A | 5/1997 | Nakamura et al. | |
| 5,646,680 A * | 7/1997 | Yajima | 348/74 |
| 5,868,666 A | 2/1999 | Okada et al. | |
| 6,120,435 A * | 9/2000 | Eino | 348/65 |
| 6,462,770 B1 * | 10/2002 | Cline et al. | 348/65 |
| 6,790,174 B2 * | 9/2004 | Kaneko et al. | 600/118 |
| 7,053,954 B1 * | 5/2006 | Canini | 348/362 |
| 7,204,803 B2 * | 4/2007 | Ueno et al. | 348/224.1 |
| 2002/0175993 A1 * | 11/2002 | Ueno et al. | 348/68 |
| 2003/0025789 A1 | 2/2003 | Saito et al. | |
| 2003/0160865 A1 * | 8/2003 | Takahashi | 348/65 |
| 2006/0132657 A1 * | 6/2006 | Lee et al. | 348/625 |

FOREIGN PATENT DOCUMENTS

| | | |
|---|---|---|
| EP | 1 258 221 A2 | 11/2002 |
| JP | 5-277065 | 10/1993 |
| JP | 10-210324 | 8/1998 |
| JP | 2002-95635 | 4/2002 |
| JP | 2002-336196 | 11/2002 |

* cited by examiner

*Primary Examiner*—John M Villecco
(74) *Attorney, Agent, or Firm*—Scully, Scott, Murphy & Presser, P.C.

(57) ABSTRACT

Illumination light supplied from an illumination light supplying unit that can selectively supply a plurality kinds of illumination lights whose wavelengths fall in different regions is supplied to an object. A signal picking up an image of the object is received by a programmable circuit unit that is programmably constructed based on circuit data, and then subjected to signal processing. A circuit data holding unit holds a plurality kinds of circuit data to be used for the programmable circuit unit. A control unit selects circuit data, which is used for the programmable circuit unit, from among all the circuit data items held in the circuit data holding unit corresponding to illumination light supplied from the illumination light supplying unit.

20 Claims, 7 Drawing Sheets

PROGRAMMABLE IMAGE PROCESSING UNIT WHICH DISPLAYS A TENTATIVE IMAGE DURING PROGRAMMING

This application claims the benefit of Japanese Application No. 2003-185715 filed on Jun. 27, 2003, the contents of which are incorporated by this reference.

BACKGROUND OF THE INVENTION

1. Field of the Invention

The present invention relates to an image processing device enabling observation under a plurality kinds of observation light.

2. Description of the Related Art

Electronic endoscopes are designed to be inserted into body cavities and the like and widely used to observe the alimentary tract including the esophagus, stomach, small intestine, and large intestine or the trachea such as lungs. The electronic endoscope is also adapted to various kinds of treatment or cure that are performed using a treatment instrument passed through a treatment instrument channel.

For example, in a field-sequential endoscope system, light emanating from a light source unit is passed through an optical filter in order to sequentially irradiate red, green, blue light and the like to an object. A monochrome image pickup device receives the lights reflected from the object. A processor (signal processing unit) performs signal processing on an output signal of the image pickup device. Eventually, a color image is displayed on a display device.

The signal processing to be performed in the processor includes color enhancement that is intended to help discover a lesion. In the color enhancement, a color is enhanced using an amount of hemoglobin contained in the mucosa of a living body as a criterion. This helps distinguish a normal mucosa from an abnormal mucosa on the basis of a difference in color.

Moreover, when an endoscope is used for diagnosis, normal observation is performed in order to display a color image, which depicts an object in the same manner as the object is seen with the naked eyes, on a monitor. In addition, self-fluorescent observation that utilizes light resulting from self-fluorescence of a living-body tissue is prevailing. In the self-fluorescent observation, the spectral characteristic of self-fluorescent light deriving from fluorescence of a living-body tissue caused with excitation light whose wavelengths range from the infrared region of the electromagnetic spectrum to the blue region thereof varies depending on whether the living-body tissue is a normal mucosa or a tumor.

Diagnosis is performed by utilizing the fact that the spectral characteristic of self-fluorescent light varies depending on whether a living-body tissue is a normal mucosa or a tumor.

An image represented by self-fluorescent light and an image represented by light reflected from a living-body tissue are assigned different colors and displayed on a monitor. Consequently, a lesion can be clearly identified based on a difference in color from a normal region.

Moreover, as disclosed in, for example, Japanese Unexamined Patent Application Publication No. 2002-95635, narrow-band light observation (or narrow-band imaging (NBI)) is adopted as observation under light whose wavelengths fall within a narrower band than the wavelengths of normal observation light. In the narrow-band light observation, the vessels in the mucosal membrane can be observed with a higher contrast.

Since the narrow-band light observation is observation under narrow-band light, an image whose color tone is different from the color tone of a normal endoscopic image is displayed. A color conversion circuit is therefore incorporated in a processor in order to adjust colors. After the color tone is converted into a color tone more helpful in distinguishing a lesion, the image is displayed on the monitor.

Moreover, infrared observation that is observation under near infrared light is popular. During infrared observation, a chemical agent called indocyanine green (ICG) to which near infrared light is absorbed is injected into the vessel. Consequently, the vascular kinetics in a submucous deep region that is not visualized by normal observation can be observed. Even during the infrared observation, if color enhancement is performed using an amount of ICG contained in the mucosa as a criterion, the vessels can be observed with a higher contrast.

The facilities for performing the foregoing normal observation, fluorescent observation, narrow-band light observation, and infrared observation may be implemented in one system by employing a lighting unit capable of switching illumination lights.

In order to reduce the scale of the circuitry of an endoscope system, as disclosed in Japanese Unexamined Patent Application Publication No. 5-277065 (Japanese Patent No. 3382973), a programmable logic element is included for each of charge-coupled devices (CCDs) incorporated in endoscopes to be connected. Thus, the same circuit is used in common in different facilities.

SUMMARY OF THE INVENTION

The present invention is an image processing device for performing image processing on an image pickup signal that represents the picked-up image of an object. The image processing device comprises:

a programmable circuit unit that performs signal processing on the image pickup signal using a circuit which is programmably constructed based on selected circuit data;

a circuit data holding unit that holds a plurality kinds of circuit data; and a control unit that controls such that a second circuit is programmably constructed by selecting, based on a directive signal that directs switching, a second circuit data that is different from first circuit data used in the first circuit, from among the circuit data items held in the circuit data holding unit.

BRIEF DESCRIPTION OF THE DRAWINGS

FIG. 1 shows the overall configuration of an endoscope system including the first embodiment of the present invention;

FIG. 2 is an explanatory diagram showing a band switching filter;

FIG. 3 is an explanatory diagram showing a rotary filter panel;

FIG. 4 shows the properties of transmittance exhibited by a normal/fluorescent observation filter and an infrared observation filter respectively;

FIG. 5 shows the property of transmittance exhibited by a narrow-band light observation filter;

FIG. 6 shows the properties of transmittance exhibited by red, green, and blue filters;

FIG. 7 shows the properties of transmittance exhibited by an excitation filter, a G' filter, and an R' filter;

FIG. 8 shows the property of transmittance exhibited by an excitation cut filter;

FIG. 9 is a flowchart describing control actions to be performed in order to switch filters in the first embodiment;

FIG. 10 shows the configuration of a color enhancement circuit constructed using a field-programmable gate array (FPGA);

FIG. 11 shows the configuration of a noise cancellation circuit constructed using the FPGA;

FIG. 12 shows the configuration of a color conversion circuit constructed using the FPGA.

DESCRIPTION OF THE PREFERRED EMBODIMENTS

Figure 1:
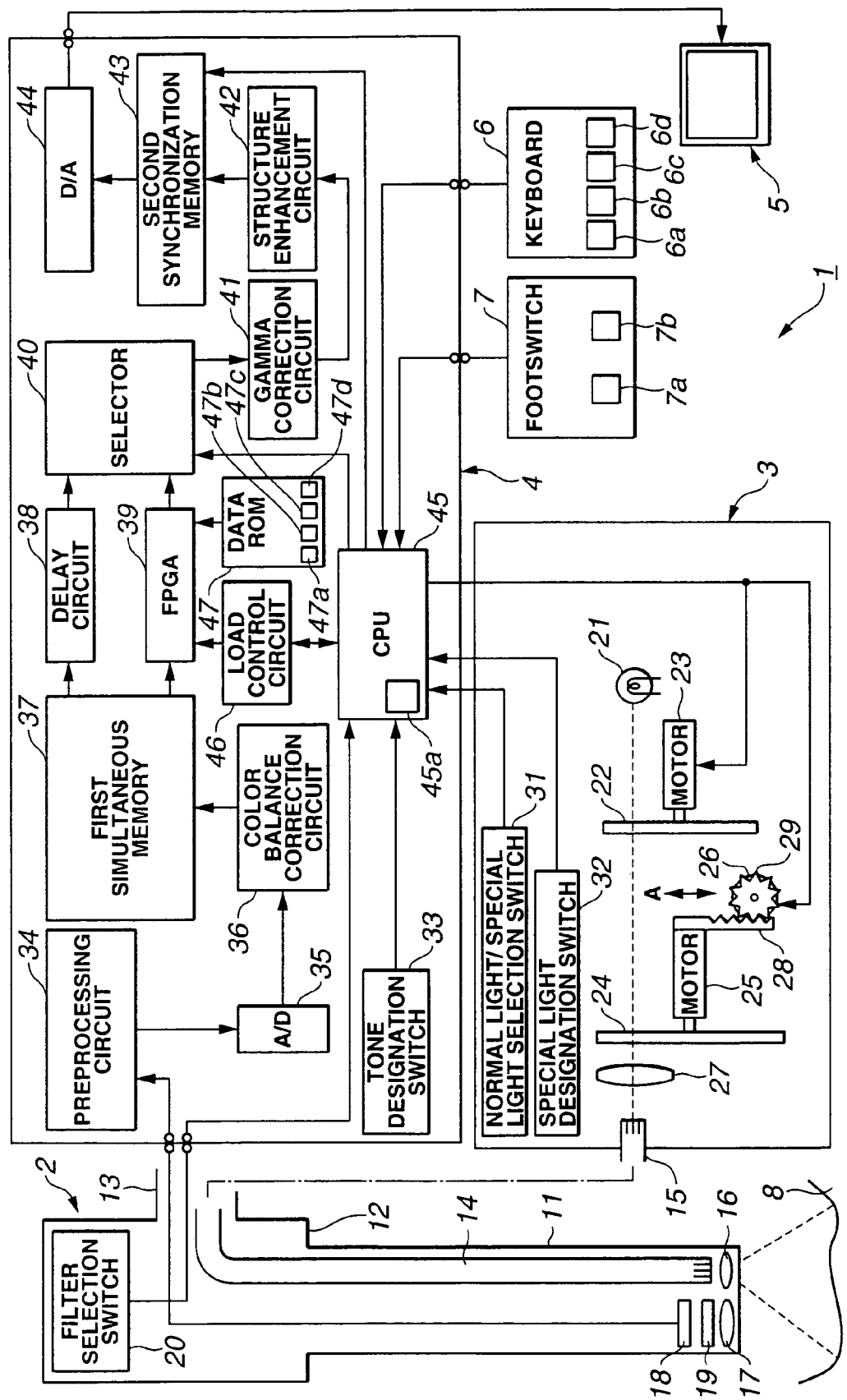
FIG. 1 to FIG. 12 are concerned with a first embodiment of the present invention.

Referring to the drawings, embodiments of the present invention will be described below.

First Embodiment

Referring to FIG. 1 to FIG. 12, a first embodiment of the present invention will be described below.

An object of the present embodiment is to provide an image processing device and an electronic endoscope system which make it possible to perform different kinds of signal processing corresponding to a plurality kinds of observation light (observation modes) using small-scale circuitry and possible to display a view image in the form of a motion picture even during construction of a programmable logic element (construction of a circuit). To begin with, the configuration of the present embodiment will be described below.

As shown in FIG. 1, an electronic endoscope system 1 including the first embodiment of the present invention comprises: an electronic endoscope (hereinafter, an endoscope) 2 that is inserted into a body cavity in order to pick up an image of an object 8 such as a lesion in the body cavity; a light source unit 3 to or from which the endoscope 2 is freely coupled or uncoupled and which generates illumination light for observation; a processor 4 to or from which the endoscope is freely coupled or uncoupled and which performs signal processing or the like on an image signal representing the picked-up image; a monitor 5 which is connected to the processor 4, to which a video signal is transmitted from the processor 4, and on which an image represented by the video signal is displayed; a keyboard 6 connected to the processor 4 and used to enter data or commands; and a footswitch 7.

The endoscope 2 comprises: an elongated insertional unit 11 that is inserted into a body cavity; an operating unit 12 disposed at the back end of the insertional unit 11; and a universal cord 13 extending from the operating unit 12.

A light guide fiber 14 by which illumination light is transmitted is run through the insertional unit 11 of the endoscope 2. The back side portion of the light guide fiber 14 is passed through the universal cord 13. A light guide connector 15 is attached to the back end of the light guide fiber 14. A user couples the light guide connector 15 freely detachably to the light source unit 3. Illumination light emanating from the light source unit 3 is introduced to the incidence end surface of the light guide connector 15.

The illumination light transmitted to the light guide fiber 14 is irradiated from a distal end surface (emission end surface), which is attached to an illumination window formed in the distal section of the insertional unit 11, through an illumination lens 16 to the object 8 in the body cavity.

An objective lens 17 is attached to an observation window (image pickup window) adjoining the illumination window. A high-sensitivity solid-state image pickup device, or more particularly, a charge-coupled device (CCD) 18 is disposed at the image-forming position of the objective lens 17. The CCD 18 photoelectrically coverts the picked-up image formed on the image pickup surface of the CCD 18. The CCD 18 can be connected to or disconnected from the processor 4 by a connector formed at an end of a signal line.

An excitation light cut filter 19 is disposed in front of the image pickup surface of the CCD 18. The excitation light cut filter 19 cuts out excitation light that is used for fluorescent observation, so that feeble fluorescent light can be introduced into the CCD 18.

Moreover, the operating unit 12 of the endoscope 2 includes a filter selection switch 20 that is used to direct switching of illumination lights to be achieved through switching of filters. A directive signal produced by the filter selection switch 20 is transmitted to a CPU 45.

The light source unit 3 comprises: a lamp 21 that is formed with a xenon lamp or the like and that radiates light whose wavelength ranges from the infrared region to the visible region; a band switching filter 22 that is disposed on the path of illumination light emanating from the lamp 21 and that limits transmitted wavelength; a motor 23 used to switch the band switching filter 22; a rotary filter panel 24 including filters that pass light of different wavelength band; a motor 25 used to rotate or drive the rotary filter panel 24; a motor 26 used to move the rotary filter panel 24 in a direction A perpendicular to the illumination optical axis; and a condenser lens 27 that concentrates light transmitted by the rotary filter panel 24 and has the light incident on the end surface of the light guide connector 15.

In this case, the motor 25 for rotating the rotary filter panel 24 has a rack 28 attached thereto. A pinion 29 that is meshed with the rack 28 is attached to the rotation shaft of the motor 26. By rotating or driving the motor 26, the motor 25 and rotary filter panel 24 are moved in the direction A perpendicular to the illumination optical axis.

Moreover, a normal light/special light switching switch 31 and a special light selection switch 32 are located at a position on, for example, a front panel of the light source unit 3 at which a user can easily manipulate the switches. Herein, the special light signifies any of fluorescent observation, narrow-band light observation, and infrared observation.

The processor 4 is designed such that a video signal will orderly flow into: a preprocessing circuit 34 that performs preprocessing on an image pickup signal received from the CCD 18; an A/D conversion circuit 35; a color balance correction circuit 36; a first simultaneous memory 37; a delay circuit 38 or a field programmable gate array (FPGA) 39 that programmably constructs a circuit; a selector 40 that selects either of the signals received from the delay circuit 38 and FPGA 39; a gamma correction circuit 41, a structure enhancement circuit 42 that is formed with a spatial filter circuit; a second simultaneous memory 43; and a D/A conversion circuit 44.

The CPU 45 that is responsible for control and the like and incorporated in the processor 4 is electrically connected to external equipment such as the endoscope 2, keyboard 6, footswitch 7, and light source unit 3, and also electrically connected to internal circuits such as a color tone designation switch 33, a load control circuit 46 and the like that are incorporated in the processor 4.

The FPGA 39 that programmably constructs a circuit has an internal memory, as well as a gate circuit, that performs logic operations. The FPGA 39 may include lookup tables or an image memory.

The load control circuit 46 is connected to be able to designate an address in a data ROM 47 in which data to be loaded into the FPGA 39 is stored. An output terminal of the data ROM 47 is connected to a data load pin in a connector included in the FPGA 39.

A total of four circuit data items corresponding to observation modes for normal observation, fluorescent observation, narrow-band light observation, and infrared observation (normal observation mode circuit data 47a, fluorescent observation mode circuit data 47b, narrow-band light observation mode circuit data 47c, and infrared observation mode circuit data 47d) are stored in the data ROM 47. Selected circuit data is loaded into the FPGA 39, whereby a circuit described by the circuit data is constructed.

The keyboard 6 includes, in addition to normal keys, four keys for use in designating normal observation, fluorescent observation, narrow-band light observation, or infrared observation, that is, a normal observation designation key 6a, a fluorescent observation designation key 6b, a narrow-band light observation designation key 6c, and an infrared observation designation key 6d. Moreover, the footswitch 7 includes switches 7a and 7b equivalent to the normal light/special light switching switch 31 and special light selection switch 32 disposed in the light source unit 3.

Figure 2:
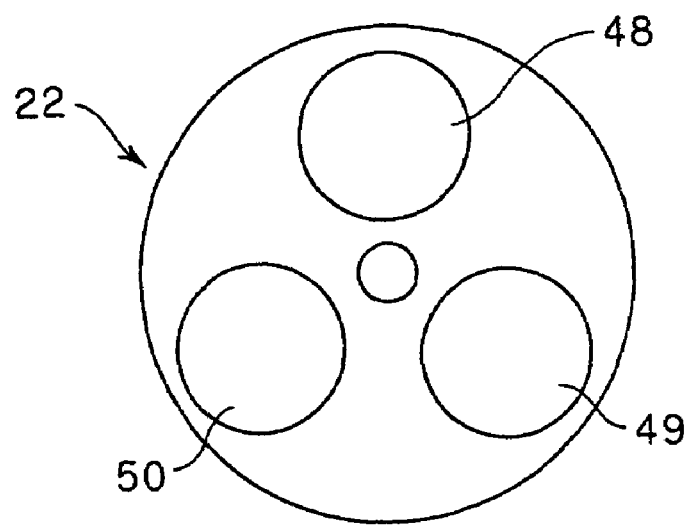

As shown in FIG. 2, the band switching filter 22 includes a normal/fluorescent observation filter 48, an infrared observation filter 49, and a narrow-band light observation filter 50.

Figure 4:
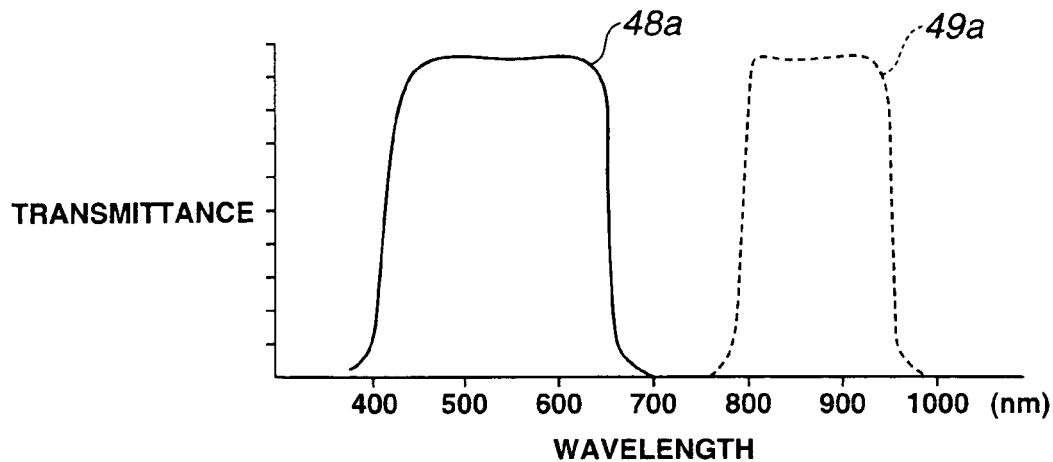
Figure 5:
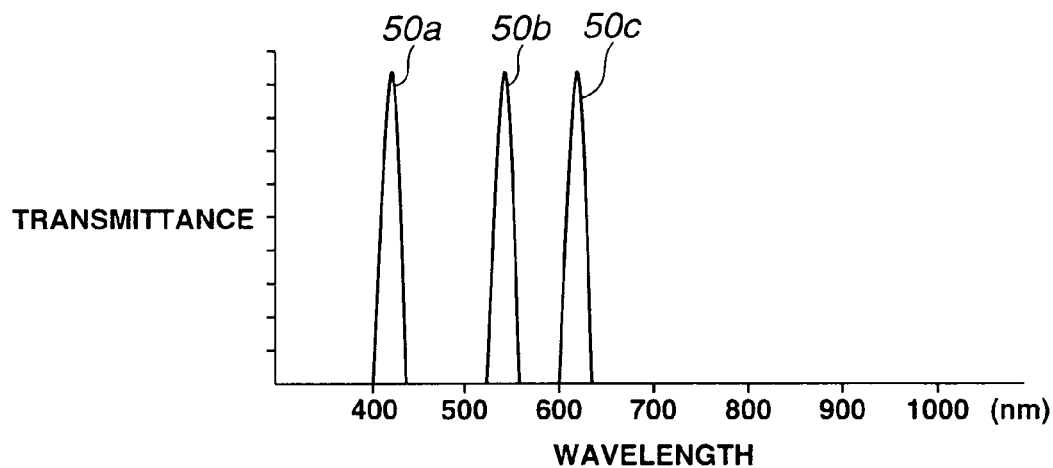

FIG. 4 and FIG. 5 show the spectral characteristics of lights transmitted by the filters. Namely, FIG. 4 shows the property of transmittance 48a exhibited by the normal/fluorescent observation filter 48 and the property of transmittance 49a exhibited by the infrared observation filter 49. FIG. 5 shows the properties of transmittance 50a, 50b, and 50c exhibited by the narrow-band light observation filter 50.

The property of transmittance 48a of the normal/fluorescent observation filter 48 is such that the normal/fluorescent observation filter 48 transmits light whose wavelength ranges from 400 nm to 660 nm. The property of transmittance of the infrared observation filter 49 is such that the infrared observation filter 49 transmits light whose wavelengths range from 790 nm to 980 nm.

As shown in FIG. 5, the narrow-band light observation filter 50 exhibits three peaks of the properties of transmittance 50a, 50b, and 50c which transmit three respective lights belonging to three discrete wavelength bands. Namely, the narrow-band light observation filter 50 exhibits the properties of transmittance 50a, 50b, and 50c of transmitting respective lights whose wavelengths range from 400 nm to 430 nm, from 530 nm to 560 nm, or from 600 nm to 630 nm.

Figure 3:
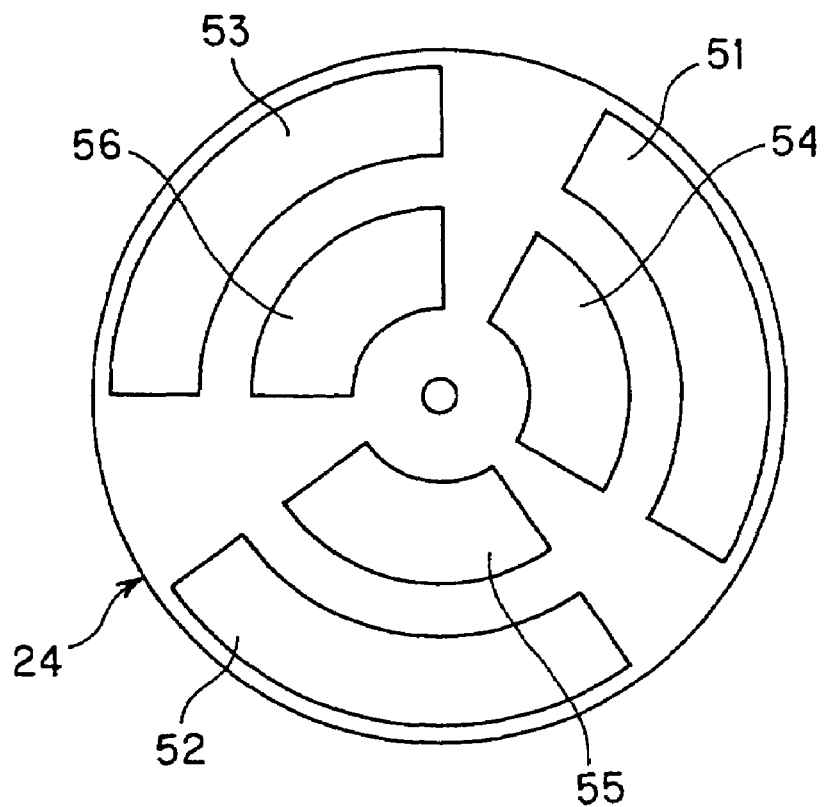

The outer circumference of the rotary filter panel 24 includes, as shown in FIG. 3, an R filter 51, a G filter 52, and a B filter 53 that transmit respective lights whose wavelengths fall within the red, green, or blue region.

The inner circumference of the rotary filter panel 24 includes a G' filter 54 that transmits light whose wavelength ranges from 540 nm to 560 nm, an excitation filter 55 that transmits excitation light whose wavelength ranges from 390 nm to 450 nm, and an R' filter 56 that transmits light whose wavelength ranges from 600 nm to 620 nm.

Figure 6:
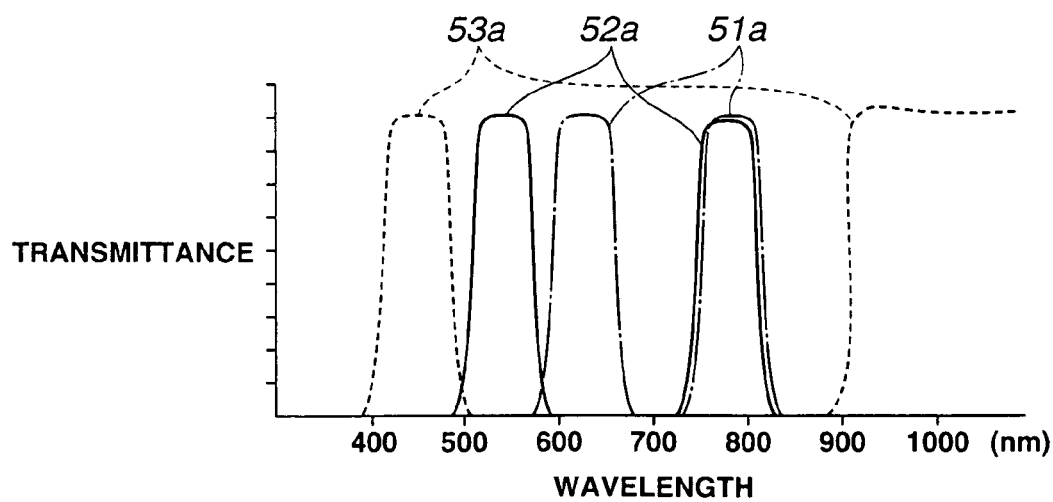
Figure 7:
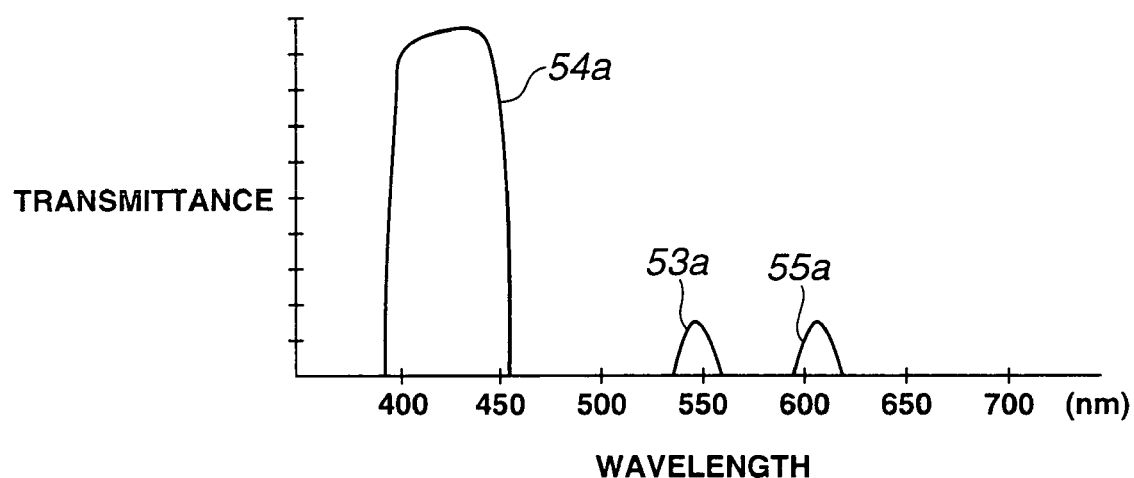

FIG. 6 and FIG. 7 show the spectral characteristics of lights transmitted by the outer and inner-circumference filters of the rotary filter panel 24. Namely, FIG. 6 shows the properties of transmittance 51a, 52a, and 53a exhibited by the R filter 51, G filter 52, and B filter 53 respectively.

As shown in FIG. 6, the outer-circumference filters 51, 52, and 53 have the properties of partially transmitting light whose wavelength falls within not only the visible region but also the near infrared region.

More specifically, the properties of transmittance 51a and 52a of the R filter 51 and G filter 52 are such that the R filter 51 and G filter 52 transmit light whose wavelength ranges from 750 nm to 820 nm. The property of transmittance 53a of the B filter 53 is such that the B filter 53 transmits light whose wavelength is equal to or larger than 900 nm.

Figure 8:
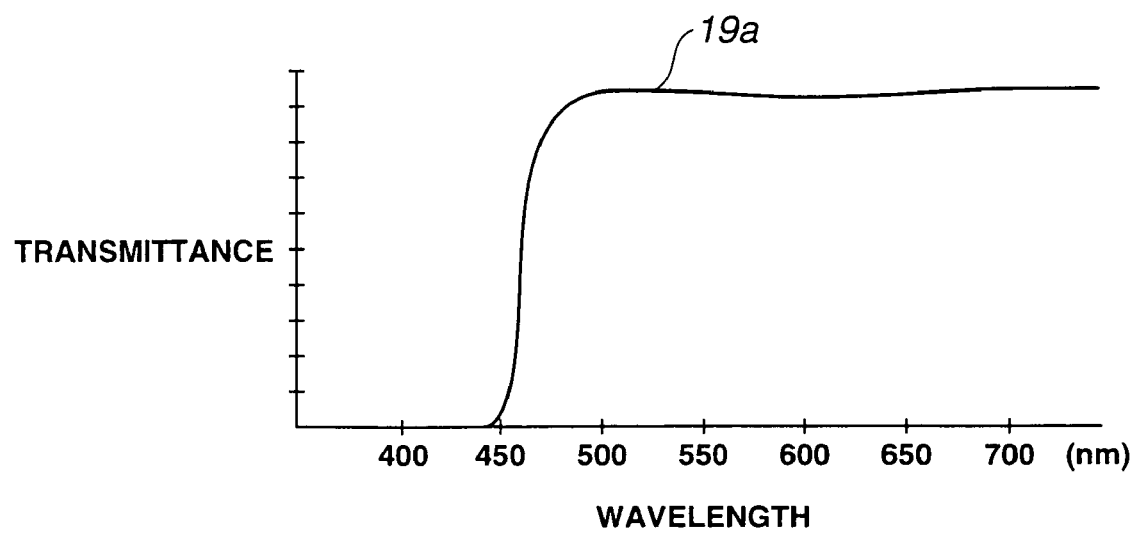

The excitation light cut filter 19 exhibits, as shown in FIG. 8, the property of transmittance 19a of intercepting light whose wavelength is equal to or smaller than 450 nm. The wavelength band transmitted by the excitation light cut filter 19 does not overlap the wavelength band transmitted by the excitation filter 55.

According to the present embodiment, the light source unit 3 introduces illumination light, which is associated with a selected one of the plurality kinds of observation modes, to the light guide fiber 14 included in the endoscope 2.

Moreover, according to the present embodiment, whichever of the observation modes is selected, once circuit data to be read from the data ROM 47 is determined (the load control circuit 46 controls loading), a circuit that performs required signal processing on a signal representing an image picked up in the observation mode can be programmably constructed by the FPGA 39. This process is controlled by the CPU 45. Moreover, a control program describing the process is stored in a memory 45a incorporated in, for example, the CPU 45.

According to the present embodiment, owing to the foregoing constituent feature, the FPGA 39 is used in common to construct a color enhancement circuit for, for example, normal observation or infrared observation or to construct a noise cancellation circuit for fluorescent observation. Thus, required signal processing is achieved despite the small-scale circuitry.

Moreover, according to the present embodiment, in addition to the FPGA 39, the delay circuit 38 is provided in combination to construct a bypass circuit that causes, for example, motion picture data to bypass the FPGA 39 and that thus enables display of a motion picture.

The selector 40 can select either a circuit programmably constructed by the FPGA 39 or the bypass circuit. When construction of a circuit constructed by the FPGA 39 is under way, motion picture data is temporarily routed to the bypass circuit. Consequently, even when construction of a circuit by the FPGA 39 is under way, a motion picture can be displayed. This leads to improved user-friendliness.

Next, the operation of the present embodiment will be described below.

Light with which an object is illuminated is radiated from the lamp 21 included in the light source unit 3. The light radiated from the lamp 21 passes through the band switching filter 22 and rotary filter panel 24. Thereafter, the light is converged by the condenser lens 27 and introduced into the light guide fiber 14 included in the endoscope 2.

The band switching filter 22 is driven to rotate by the motor 23 in response to a filter selection directive signal sent from the CPU 45. During normal observation or fluorescent observation, the normal/fluorescent observation filter 48 is inserted into the path of illumination light. During narrow-band light observation, the narrow-band light observation filter 50 is inserted into the path of illumination light. During infrared observation, the infrared observation filter 49 is inserted into the path of illumination light.

During normal observation, narrow-band light observation, or infrared observation, any of the outer-circumference filters of the rotary filter panel 24 is inserted into the optical axis of illumination light. The rotary filter panel 24 is driven to rotate at a predetermined speed by the motor 25, whereby the R filter 51, G filter 52, and B filter 53 are sequentially inserted into a light path.

Owing to the combined use of the rotary filter panel 24 and band switching filter 22, red, green, and blue lights are transmitted during normal observation. Lights whose wavelength ranges from 400 nm to 430 nm, 530 nm to 560 nm, or 600 nm to 630 nm is transmitted during narrow-band light observation. Lights whose wavelength ranges from 790 nm to 820 nm or 900 nm to 980 nm is transmitted during infrared observation.

In order to acquire an image formed by feeble fluorescent light with a long exposure period, the motor 25 is rotated at a slower speed during fluorescent observation than in the other observation modes. Moreover, during fluorescent observation, the rotary filter panel 24 is moved in a direction A perpendicular to the path of illumination light by the motor 26 in response to a filter selection directive signal sent from the CPU 45. Consequently, any of the inner-circumference filters is inserted into the path of illumination light.

When the inner-circumference filters are sequentially inserted, lights whose wavelength ranges from 540 nm to 560 nm, 390 nm to 450, or 600 nm to 620 nm is sequentially emitted from the light source unit 3. The light whose wavelengths range from 390 nm to 450 nm is excitation light for use in exciting self-fluorescence of a living-body tissue.

Light incident on the light guide fiber 14 included in the endoscope 2 is irradiated to the object 8 such as the alimentary tract through the illumination window formed in the distal section of the endoscope 2. Light scattered, reflected, or radiated from the object 8 forms an image on the CCD 18 by the objective lens 17 disposed on the observation window formed in the distal section of the endoscope 2, and the image is photoelectrically converted to be picked up.

The excitation light cut filter 19 is located in front of the CCD 18, and works to intercept excitation light whose wavelength ranges from 390 nm to 450 nm and to extract fluorescent light. The CCD 18 is driven by a CCD drive circuit, which is not shown, synchronously with the rotation of the rotary filter panel 24. Image signals representing respective illumination lights that have passed through the R filter 51, G filter 52, and B filter 53 of the rotary filter panel 24 are sequentially received by the processor 4.

The image signals received by the processor 4 are first received by the preprocessing circuit 34. The preprocessing circuit 34 performs correlation double sampling (CDS) or the like, and the image signals are taken out.

The signals sent from the preprocessing circuit 34 are converted from an analog form into a digital form by the A/D conversion circuit 35. The signals sent from the A/D conversion circuit 35 are received by the color balance correction circuit 36.

The color balance correction circuit 36 adjusts the amplification factors for the signals such that when an object image serving as a reference is picked up, the object image will be displayed on the monitor 5 in predetermined colors. Thereafter, the resultant signals are temporarily stored in the first simultaneous memory 37. Image data items sequentially stored in the first simultaneous memory 37 are read simultaneously with one another, whereby the simultaneity of the field-sequential images is performed.

The image data resulting from the synchronization is received by the delay circuit 38 and FPGA 39. The delay circuit 38 is formed with a memory and used to match the timing of a received signal with the timing of a signal that passes through the FPGA 39, that is, to delay the received signal by the same time interval as the time interval required for the signal sent to the FPGA 39 to pass through the FPGA 39.

The output signal of the delay circuit 38 and that of the FPGA 39 are received by the selector 40. The selector 40 selects either the signal received from the delay circuit 38 or the signal received from the FPGA 39, and changes the simultaneous signal into field-sequential signals. The resultant field-sequential signals are then transmitted to the gamma correction circuit 41.

Herein, the simultaneous signal is changed to the field-sequential signals so as to reduce the scales of the gamma correction circuit 41 and structure enhancement circuit 42. Specifically, when the selector 40 selects the signal received from the first simultaneous memory 37, the selector 40 time-sequentially reads the components of the signal so as to thus frame-sequence the received signals.

The gamma correction circuit 41 performs conversion processing for the purpose of correcting the gamma characteristic of an image to be displayed on the monitor 5. Moreover, the structure enhancement circuit 42 performs signal processing to enhance the contour of an image. Thereafter, the signals having undergone the enhancement are received by the second simultaneous memory 43.

The simultaneity of signals is performed again in the second simultaneous memory 43. A resultant signal is converted into an analog form by the D/A conversion circuit 44, and transmitted to the monitor 5. An image picked up by the CCD 18 is then displayed on the display surface of the monitor 5.

When a user manipulates any of the filter selection switch 20 on the endoscope 2, the keyboard 6, the footswitch 7, and the switches 31 and 32 on the light source unit 3, switching of observation lights (although lights actually switched are illumination lights, since observation lights are switched accordingly, the expression "switching of observation lights" is adopted) is achieved.

The keyboard 6 includes the keys 6a to 6D that are associated with normal observation, fluorescent observation, narrow-band light observation, and infrared observation. A user selects a desired observation mode by directly manipulating any of the keys, whereby an associated directive signal is received by the CPU 45. In response to the directive signal, the CPU 45 switches observation lights.

When the filter selection switch 20 on the endoscope 2 is pressed, every time a user presses the switch 20, the CPU 45 sequentially switches observation lights in the order of normal observation, fluorescent observation, narrow-band light observation, infrared observation, normal observation, etc.

When the normal light/special light switching switch 31 on the light source unit 3 (or the equivalent switch 7a on the footswitch 7) is pressed, if the mode attained before the switch is pressed is any of the fluorescent observation, narrow-band light observation, and infrared observation modes, the CPU 45 will change the mode to the normal observation mode.

If the mode attained before the switch is pressed is the normal observation mode, the CPU 45 will change the mode to any of the fluorescent observation, narrow-band light observation, and infrared observation modes. In this case, to whichever of the fluorescent observation, narrow-band light observation, and infrared observation modes the normal observation mode is switched can be determined using the special light selection switch 32.

Every time a user presses the special light selection switch 32, three special light observation modes are sequentially switched over in the order of fluorescent observation, narrow-band light observation, infrared observation, fluorescent observation, etc. Thus, the user can select any of the three special light observation modes.

If the mode attained before the special light selection switch 32 is pressed is the normal observation mode, the CPU 45 does not switch observation lights. An indicator LED that is not shown informs a user of the fact that the special light observation modes have been changed. If the mode attained before the special light selection switch 32 is pressed is not the normal observation mode, the CPU 45 actually switches observation lights.

Figure 9:
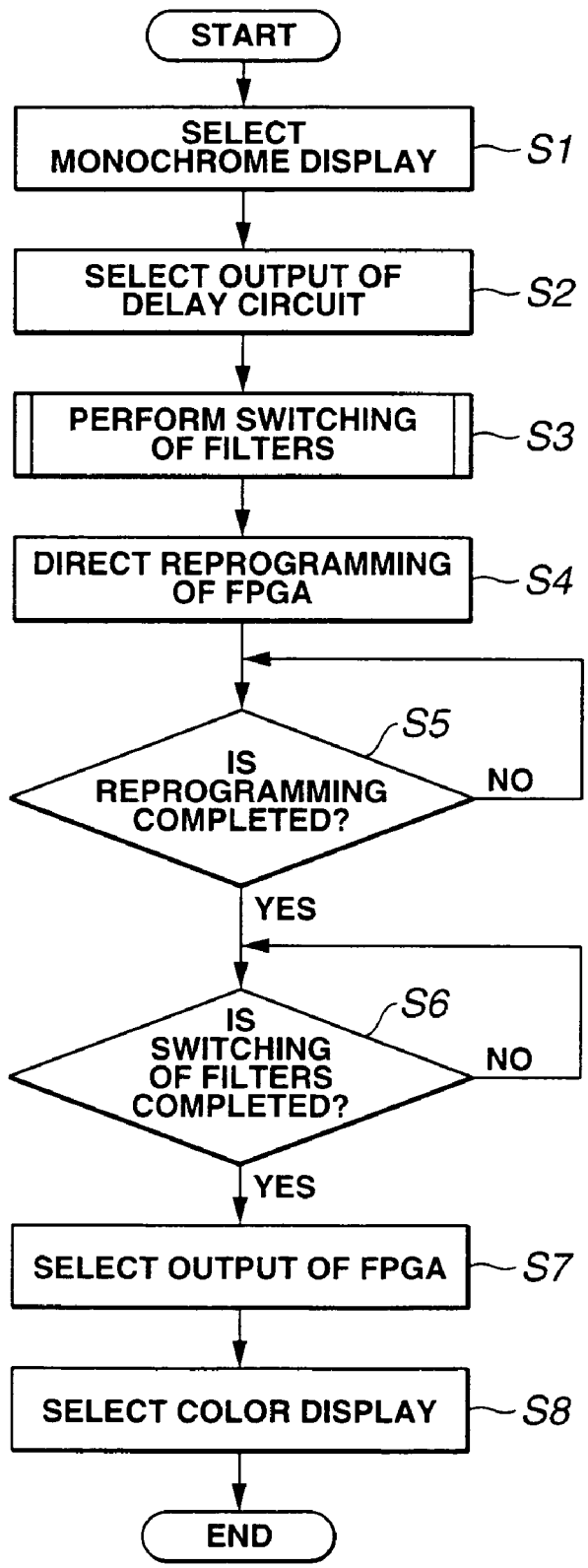

FIG. 9 describes the details of a process of switching observation lights that are executed by the CPU 45 according to a control method described in a control program stored in the memory 45a.

The image processing control method according to which the CPU 45 executes the control process as described in FIG. 9 will be briefed below.

If a state of currently selected illumination light and a state of a circuit constructed with the FPGA 39 associated with the light and being in operation is changed to another state directed to perform image processing according to the switching direction, the CPU 45 controls the FPGA 39 to construct a new circuit having a different image processing capability.

While construction of a new circuit is under way, the CPU 45 transmits a tentative image (a monochrome motion picture in the present embodiment). Thus, an image is displayed on the monitor 5 without fail. When construction of a new circuit through the FPGA 39 is completed, the CPU 45 transmits an image produced by the constructed new circuit to the display means. Owing to this control process, even when construction of a circuit through the FPGA 39 is under way, an event that no image is displayed can be prevented. A description will be made in conjunction with FIG. 9 below.

When the CPU 45 receives a switching directive entered by a user, the CPU 45 controls the second simultaneous memory 43 to assign the same signal (green color signal) to all the channels for red, green, and blue signals to be transmitted to the monitor 5. Consequently, a monochrome image is transmitted to the monitor (see step S1).

At the next step S2, the CPU 45 causes the selector 40 to select an image signal received from the delay circuit 38, and prevents an image signal from passing through the FPGA 39. Namely, the CPU 45 selects the image signal having passed through the delay circuit 38.

At the next step S3, the CPU 45 directs the load control circuit 46 to load data into the FPGA for the purpose of reconfiguring of the FPGA (see step S4), and thus reconfigures the FPGA 39.

The load control circuit 46 designates an address in the data ROM 47 associated with observation light, and reads circuit data, which is loaded into the FPGA 39, from the data ROM 47. Consequently, the circuit data read from the data ROM 47 corresponding to the observation light is loaded into the FPGA 39.

The CPU 45 judges from the action of the load control circuit 46 whether configuring is completed (step S5). Specifically, the CPU 45 waits until a signal confirming that loading of data is completed is sent from the FPGA 39. Moreover, the CPU 45 waits for completion of switching of filters at step S6. After switching of filters is completed, the CPU 45 causes the selector 40 to select an output of the FPGA 39 at step S7.

When the CPU 45 judges whether switching of filters is completed, the CPU 45 may judge from a switching completion signal received from the light source unit 3. Otherwise, the CPU 45 may judge from an output signal of a timer that is set to a time longer than the time required to complete switching of filters.

At the next step S8, the CPU 45 controls the second simultaneous memory 43 such that a color image will be retransmitted.

According to the present embodiment, the bypass circuit that causes a signal to bypass the FPGA 39 into which data is being loaded is included in order to transmit a tentative image through the bypass circuit. Thus, even when reprogramming of the FPGA 39 is under way, a motion picture is displayed for continuous observation.

An image resulting from image processing performed by the FPGA 39 cannot be displayed for a short period of time during which an image signal is passing through the bypass circuit. However, during the period, an image whose color tone is not normal is displayed because filters are being switched. Therefore, no particular problem occurs.

Moreover, according to the present embodiment, a motion picture can be seen. Therefore, the movement of the endoscope 2 can be checked even during switching of filters. User-friendliness is ensured. Moreover, by using a monochrome image during switching of filters, a disorder in the color tone of an image caused by the switching of filters can be made indiscernible.

Figure 10:
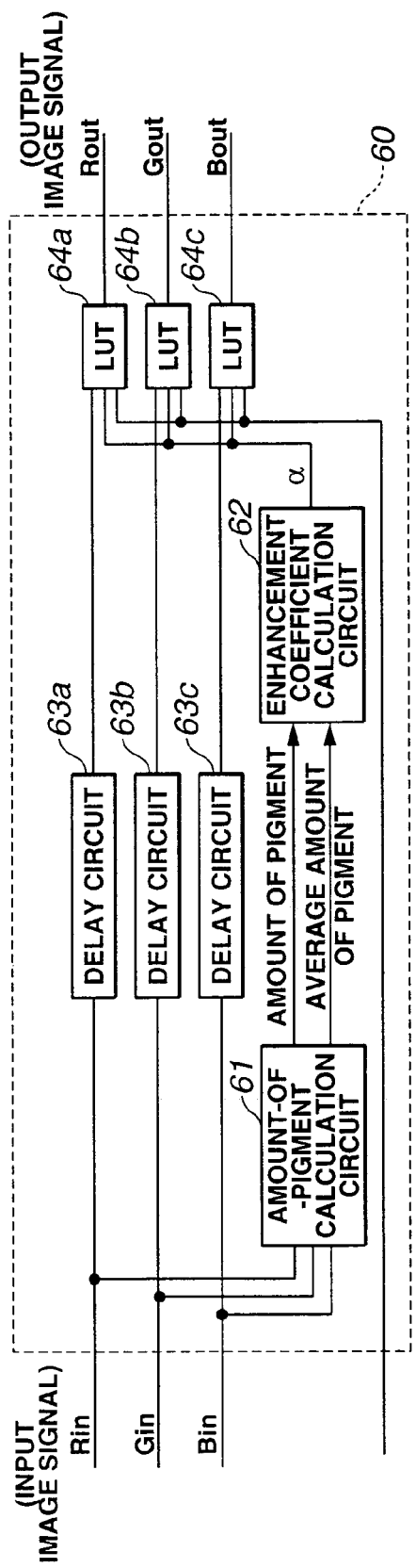

FIG. 10 shows an example of the configuration of a color enhancement circuit 60 constructed in the FPGA 39 during normal observation or infrared observation.

Based on an input image signal (more particularly, a signal Rin, Gin, or Bin), an amount-of-pigment calculation circuit 61 included in the color enhancement circuit 60 calculates an amount of pigment. The amount-of-pigment calculation circuit 61 calculates an amount of hemoglobin from each pixel value during normal observation, or calculates an amount of ICG from each pixel value during infrared observation.

The amount of hemoglobin, IHb, is calculated according to the following expression:

$$IHb=\log(R/G)$$

The amount of ICG, IIcg, is calculated according to the following expression:

$$IIcg=\log(B/R)$$

Moreover, the amount-of-pigment calculation circuit 61 not only calculates the amount of pigment (amount of hemoglobin or ICG) from each pixel value but also calculates an average amount of pigment (an average of amounts of pigments) from the values of pixels constituting one image frame.

The amounts of pigment and the average amount of pigment calculated by the amount-of-pigment calculation circuit 61 are received by an enhancement coefficient calculation circuit 62. The enhancement coefficient calculation circuit 62 calculates an enhancement coefficient on the basis of a difference between each amount of pigment and the average amount of pigment.

For normal observation (when an amount of hemoglobin, IHb, is calculated), the enhancement coefficient $\alpha$ for each pixel is calculated according to the following expression:

$$\alpha=IHb-Ave(IHb)$$

where Ave(IHb) denotes an average of amounts of hemoglobin as described later. For infrared observation (when an amount of ICG is calculated), IIcg is substituted for IHb in the above expression.

Ave(IHb) in the above expression denotes an average of amounts of hemoglobin calculated from the values of the respective pixels constituting one image frame. Herein, a difference between an amount of pigment calculated from each pixel value and the average of amounts of pigment calculated from the values of the respective pixels constituting one frame is calculated. Consequently, even an image whose color distribution is distorted can be enhanced effectively.

Moreover, the signal Rin, Gin, or Bin serving as an input image signal is delayed by a delay circuit 63a, 63b, or 63c. Thereafter, the signal is received by a lookup table (LUT) 64a, 64b, or 64c.

In other words, the image signal having the timing thereof adjusted while passing through the delay circuit 63a, 63b, or 63c, the enhancement coefficient α, and a color tone designation level specified by the CPU 45 are respectively received by the lookup table 64a, 64b, or 64c. Consequently, color enhancement is performed on each pixel on the basis of the received data and an amount of pigment.

The color enhancement is achieved according to the following expression:

$$Rout = Rin \times exp(h \times kR \times \alpha)$$

$$Gout = Gin \times exp(h \times kG \times \alpha)$$

$$Bout = Bin \times exp(h \times kB \times \alpha)$$

where Rin, Gin, or Bin denotes an input image signal of red, green, or blue respectively. Rout, Gout, or Bout denotes an output image signal of red, green, or blue respectively. KR, kG, or kB denotes a coefficient which is determined with the absorbency of pigment into each color and whose value varies depending on whether an amount of hemoglobin is calculated or an amount of ICG is calculated.

h denotes a coefficient indicating the degree of enhancement. The h value is determined by means of the CPU 45 according to a designation level entered using the color tone designation switch 33.

When the color enhancement is performed based on an amount of hemoglobin, an image expressing an apparent increase in the amount of hemoglobin is produced. When the color enhancement is performed based on an amount of ICG, an image expressing an apparent increase in the amount of ICG is produced.

The circuitry is the same irrespective of whether normal observation or infrared observation is performed. However, the absorbency of pigment is different from light to light. Therefore, the data items of the lookup tables cannot be used in common between normal observation and infrared observation.

According to the present embodiment, even when normal observation and infrared observation are switched, the FPGA 39 is reconfigured in order to construct required lookup tables 64a, 64b, and 64c. Therefore, the scale of circuitry can be minimized. Moreover, since the lookup tables 64a, 64b, and 64c are incorporated in the FPGA 39, compared with a ROM is disposed outside, fast access is enabled.

Figure 11:
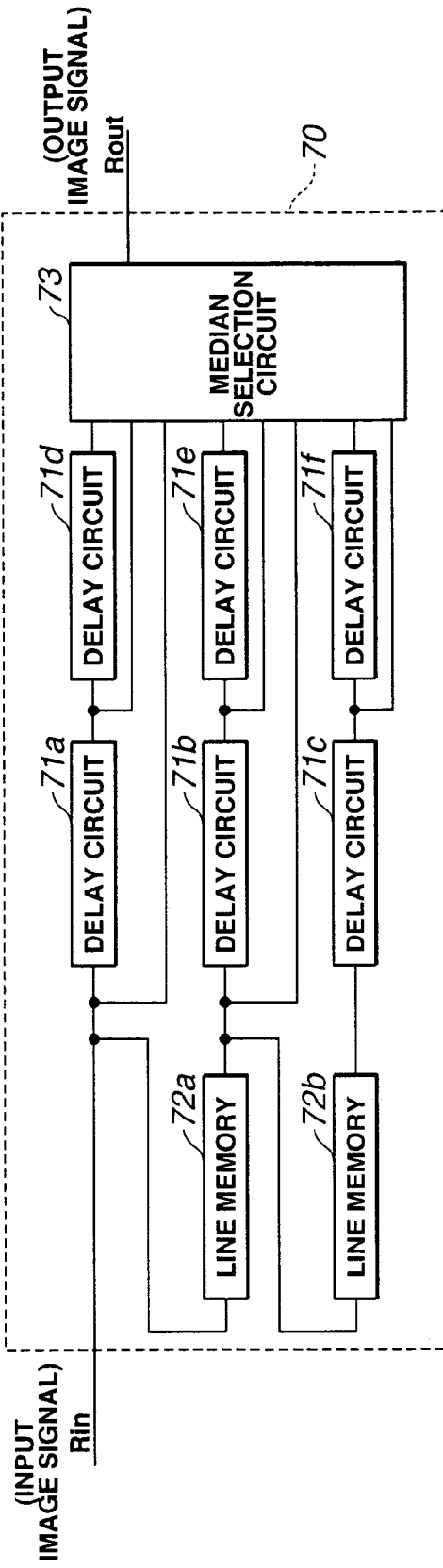

FIG. 11 shows an example of the configuration of a noise cancellation circuit 70 constructed in the FPGA 39 during fluorescent observation.

The noise cancellation circuit 70 includes a 3×3 median filter. Owing to delay circuits 71 (more particularly, 71a to 71f) for delaying a signal by a time equivalent to the cycle of one clock and owing to line memories 72 (more particularly, 72a and 72b) for delaying a signal by a time, which is required to treat pixels constituting almost one line, the values of nine pixels around a pixel concerned are received by a median selection circuit 73.

For example, an input image signal Rin is received by the median selection circuit 73 as it is. Moreover, the signal Rin is delayed by a time required to treat one pixel by the delay circuit 71a, and then received by the median selection circuit 73. The signal delayed by the time required to treat one pixel is further delayed by the time required to treat one pixel by the delay circuit 71b, and received by the median selection circuit 73.

Likewise, the input signal Rin is delayed by the time required to treat pixels constituting almost one line by the line memory 72a, and then received by the median selection circuit 73. The signal is further delayed by the time required to treat one pixel, and a time required to treat two pixels by the delay circuits 71a and 71b respectively, and then received by the median selection circuit 73.

The signal delayed by the time required to treat pixels constituting almost one line by the line memory 72a is delayed by the time required to treat pixels constituting almost one line by the line memory 72b, and then received by the median selection circuit 73. Moreover, the signal is delayed by the time required to treat one pixel, and the time required to treat two pixels by the delay circuits 71a and 71b respectively, and then received by the median selection circuit 73.

Figure 12:
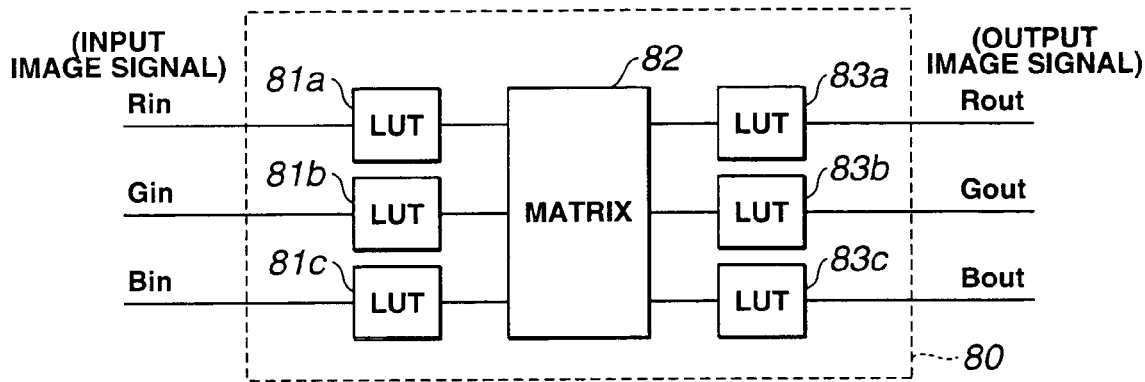

The median selection circuit 73 selects a pixel whose value is a median of the values of nine neighboring pixels, and transmits it. FIG. 11 shows only the circuit elements that treat the red signal. The same applies to the green and blue signals. FIG. 12 shows the configuration of a color conversion circuit 80 constructed in the FPGA 39 during narrow-band light observation.

In the color conversion circuit 80, an input image signal Rin, Gin, or Bin passes through a lookup table 81a, 81b, or 81c, and undergoes an arithmetic operation performed by a matrix circuit 82. The resultant signal is then transmitted via a lookup table 83a, 83b, or 83c.

The arithmetic operation performed by the matrix circuit 82 is expressed as follows:

$$Rout = a1 \cdot Rin + b1 \cdot Gin + c1 \cdot Bin$$

$$Gout = a2 \cdot Rin + b2 \cdot Gin + c2 \cdot Bin$$

$$Bout = a3 \cdot Rin + b3 \cdot Gin + c3 \cdot Bin$$

Where a, b, and c denote coefficients and a plurality of sets of values of coefficients are stored in a memory that is not shown. Any of the sets of values is selected based on a color tone designation level entered using the color tone designation switch 33 by means of the CPU 45. As this, the color tone designation switch 33 is used to designate a color enhancement level for normal observation or infrared observation and also used to select the values of the coefficients that are employed in the arithmetic operation performed by the matrix circuit during narrow-band light observation.

The designated levels are stored in the CPU 45 in association with the respective observation modes. When observation modes are switched, a stored level is designated accordingly. The lookup tables 81 and 83 are used for adjustment or used to compress or convert colors, which are not supported by the monitor 5, into colors that can be displayed.

According to the present embodiment, the FPGA 39 is employed. Any other programmable logic device (PLD) will do.

Moreover, observation lights to be switched are not limited to self-fluorescent light, narrow-band light, and infrared light. Alternatively, fluorescent light caused by a chemical agent that can be administered to a human body or light having undergone the Raman effect will do.

Moreover, the present invention is not limited to the field-sequential type endoscope system 1, but may be adapted to a simultaneous type endoscope system.

Moreover, as described in Japanese Unexamined Patent Application Publication No. 10-210324, the degree of color enhancement to be performed during normal observation or infrared observation may be adjusted based on the magnitude of a feature of an image.

Moreover, the FPGA 39, load control circuit 46, and data ROM 47 may be mounted on an independent substrate other than a substrate on which the other circuit elements are mounted. The substrate may be able to be inserted into or pulled out of the processor 4 (or may be attachable to or detachable from the processor 4), whereby a facility for performing image processing such as color conversion can be provided for a user as an extension facility of the processor 4.

Moreover, preferably, a user can assign various facilities to the switches disposed on the endoscope 2 or footswitch 7.

The present embodiment provides advantages described below.

According to the present embodiment, a programmable logic element is reconfigured during switching of filters along with switching of observation lights. Different kinds of signal processing associated with a plurality kinds of observation lights can be achieved despite a small scale of circuitry.

Moreover, according to the present embodiment, while a logic element is being configured to perform image processing, a signal is transmitted via a bypass circuit that causes the signal to bypass the logic element. Consequently, even when configuring of the programmable logic element is under way, a view image can be seen in the form of a motion picture.

Second Embodiment

Next, referring to FIG. 13, a second embodiment of the present invention will be described below.

An object of the present embodiment is to provide an image processing unit that can perform different kinds of signal processing associated with a plurality kinds of observation lights despite a small scale of circuitry and that enables display of a view image in the form of a still image even during configuring of a programmable logic element.

The present embodiment has the same hardware configuration as the first embodiment. However, the control programs stored in the memory 45a of the CPU 45 are different from those employed in the first embodiment. According to the present embodiment, as described below, while a circuit is constructed using the FPGA 39 or when observation lights are switched, the CPU 45 extends control so as to display a still image.

Next, the operation of the present embodiment will be described below.

The present embodiment is different from the first embodiment in a point of switching of observation lights.

Figure 13:
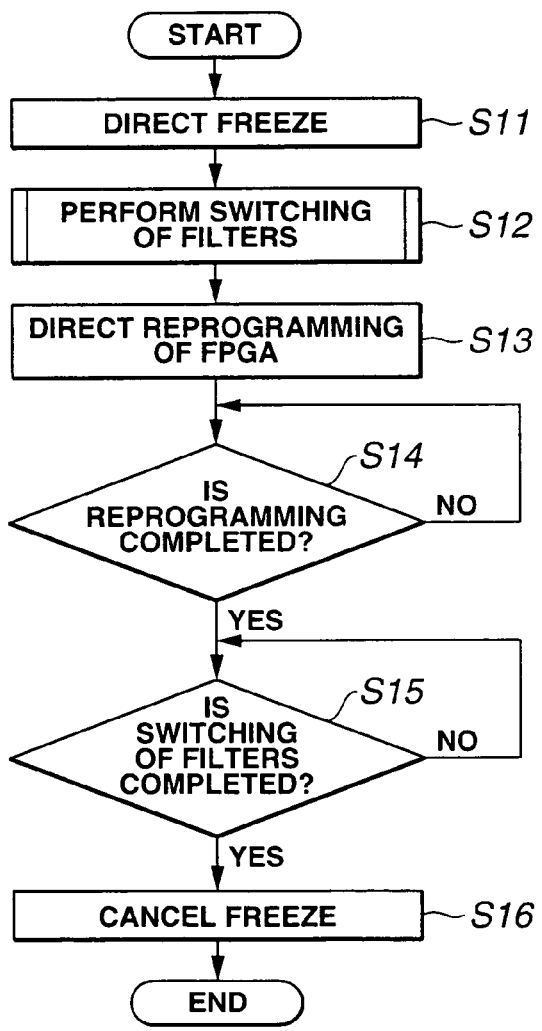
FIG. 13 is a flowchart describing control actions to be performed in order to switch filters in a second embodiment of the present invention.

FIG. 13 describes control actions to be performed by the CPU 45 for the purpose of switching of observation lights.

First, when switching of observation lights is directed, the CPU 45 controls the second simultaneous memory 43 at step S11 so as to inhibit writing of data in the second simultaneous memory 43. Thus, image data written immediately before writing is inhibited is repeatedly read out, that is, a frozen still image is transmitted.

At step S12, the CPU 45 transmits a filter selection directive signal to each of the motor 23 and motor 26 so as to switch to predetermined observation light.

At this time, at step S13, the CPU 45 directs the load control circuit 46 to reconfigure the FPGA. Thus, the FPGA 39 is reconfigured.

The load control circuit 46 designates an address in the data ROM 46 associated with the observation light, and reads circuit data that is to be loaded into the FPGA 39. Consequently, the circuit data associated with the observation light and read from the data ROM 47 is loaded into the FPGA.

At step S14, the CPU 45 judges from a load completion signal received from the load control circuit 46 whether reconfiguring has been completed.

After the CPU 45 receives the load completion signal, the CPU 45 judges at step S15 whether switching of filters has been completed. After switching of filters is completed, the CPU 45 controls the second simultaneous memory 43 to cease the freeze mode. Thus, a motion picture is retransmitted (step S16).

As mentioned above, according to the present embodiment, an image is frozen during loading of data into the FPGA 39. Consequently, even during configuring of the FPGA 39, a color still image can be viewed for observation. A disorder in an image deriving from switching of filters does not occur.

Moreover, during reconfiguring of the FPGA 39, a motion picture cannot be viewed. However, since reconfiguring of the FPGA 39 may be performed during switching of filters, an examination time will be saved owing to the reconfiguring of the FPGA 39.

The present embodiment provides advantages described below.

According to the present embodiment, a programmable logic element is reconfigured during switching of filters along with switching of observation lights. Different kinds of signal processing associated with the plurality kinds of observation lights respectively can be achieved despite a small scale of circuitry.

Moreover, according to the present embodiment, during reconfiguring of a logic element that performs image signal processing, an image is frozen in a stage that is located closer to an output stage than to the logic element. Consequently, even during reconfiguring of the programmable logic element, a still image devoid of a disorder can be viewed for observation.

As described above, according to the present invention, different kinds of signal processing associated with a plurality kinds of observation lights respectively can be achieved despite a small scale of circuitry.

The preferred embodiments of the present invention have been described with reference to the accompanying drawings. It should be understood that the present invention is not limited to the precise embodiments but a person skilled in the art can make various changes or modifications without departing from the spirit or scope of the invention defined in the appended claims.

What is claimed is:

1. An image processing unit for performing image processing on a signal that represents the picked-up image of an object, comprising:

a programmable circuit unit that is reconfigured based on selected circuit data in order to construct a circuit which performs signal processing on the image pickup signal;

a circuit data holding unit that holds a plurality kinds of circuit data; and a control unit that controls such that a first circuit is programmably constructed by selecting, based on a directive signal that directs switching, a first circuit data that is different from a second circuit data used in a second circuit, from among the circuit data items held in the circuit data holding unit, and controls such that a tentative image is outputted when the second circuit is being programmably constructed;

wherein after the first circuit data is selected from among the circuit data items held in the circuit data holding unit, when the programmable circuit unit is reconstructed based on the first circuit data in order to construct the first circuit, the control unit transmits the tentative image.

2. The image processing unit according to claim 1, wherein the tentative image is a frozen image produced by the second circuit and then stored.

3. The image processing unit according to claim 1, wherein the tentative image is produced by causing an image signal to bypass the programmable circuit unit.

4. The image processing unit according to claim 1, further comprising an illumination light supplying unit that generates illumination light to be supplied to an object, wherein the illumination light supplying unit selectively supplies a plurality kinds of illumination lights whose wavelengths fall within different regions of the electromagnetic spectrum.

5. The image processing unit according to claim 4, wherein the control unit changes the illumination light to be supplied to the object in response to a switching directive signal.

6. The image processing unit according to claim 1, wherein the programmable circuit unit is realized with a field programmable gate array or a programmable logic device.

7. An image processing device for performing image processing on a signal that represents the picked-up image of an object picked up under illumination light selectively supplied to the object from an illumination light supplying unit capable of supplying a plurality kinds of illumination lights whose wavelengths fall within different regions of the electromagnetic spectrum, comprising:

a programmable circuit unit that performs signal processing on the image pickup signal by a circuit that is programmably constructed based on circuit data;

a circuit data holding unit that holds a plurality kinds of circuit data; and a control unit that selects a piece of circuit data, which is used for the programmable circuit unit, from among the plurality kinds of data items held in the circuit data holding unit corresponding to illumination light selectively supplied from the illumination light supplying unit, the control unit controlling such that a tentative image is outputted when the programmable circuit unit is being programmably constructed based on the piece of circuit data;

wherein after the circuit data is selected from among the circuit data items held in the circuit data holding unit, when the programmable circuit unit is reconstructed based on the circuit data in order to construct the circuit, the control unit transmits the tentative image.

8. The image processing unit according to claim 7, further comprising an illumination light selection directing block unit that directs switching of the plurality kinds of illumination light.

9. The image processing device according to claim 8, wherein the control unit reconstructs the programmable circuit unit during switching of the illumination lights.

10. The image processing device according to claim 9, further comprising a frozen image circuit unit that produces a frozen image during the reconstruction of the programmable circuit unit.

11. The image processing device according to claim 7, wherein: the circuit data items held in the circuit data holding unit relate to circuits having different capabilities; and the control unit selects circuit data relevant to a circuit whose capability is associated with illumination light to be supplied from the illumination light supplying unit.

12. The image processing device according to claim 7, further comprising: a bypass block unit that causes an image pickup signal to bypass the programmable circuit unit; and an image selecting unit that selects as a display image either of the first image received from the programmable circuit unit or the second image received through the bypass block unit.

13. The image processing device according to claim 12, wherein the bypass block unit has a capability of delaying a signal by a time equivalent to a delay time occurring in the programmable circuit unit.

14. The image processing device according to claim 7, further comprising an observation mode selecting unit that selects a desired observation mode from among the plurality kinds of observation modes, wherein:

the control unit switches the illumination lights in response to a directive of selection issued from the observation mode selecting unit.

15. The image processing device according to claim 7, wherein the programmable circuit unit serves as a circuit dedicated to color enhancement or noise cancellation.

16. An image processing device comprising:

an illumination light supplying unit that selectively supplies a plurality kinds of illumination lights whose wavelengths fall in different regions of the electromagnetic spectrum;

a programmable circuit unit that programmably performs, by a circuit that is programmably constructed based on circuit data, signal processing on an image pickup signal of an object to which illumination light is supplied from the illumination light supplying unit;

a circuit data holding unit that holds a plurality kinds of circuit data; and a control unit that selects a piece of circuit data, which is used for the programmable circuit unit, from among the plurality kinds of circuit data items held in the circuit data holding unit according to illumination light supplied from the illumination light supplying unit, the control unit controlling such that a tentative image is outputted when the programmable circuit unit is being programmable constructed based on the piece of circuit data;

wherein after the circuit data is selected from among the circuit data items held in the circuit data holding unit, when the programmable circuit unit is reconstructed based on the circuit data in order to construct the circuit, the control unit transmits the tentative image.

17. The image processing device according to claim 16, wherein the illumination light supplying unit supplies first illumination light whose wavelength falls within the visible region and also supplies second illumination light whose wavelength band is different from that of the first illumination light.

18. The image processing device according to claim 17, wherein the illumination light supplying unit supplies as the second illumination light excitation light needed for fluorescent observation, infrared light, or narrow-band light.

19. An image processing control method for performing image processing on an signal, which represents an image pickup signal of an object, using a programmable circuit unit that is programmably constructed, comprising:
- a first control step of starting reconstructing the programmable circuit unit, which has been constructed based on second circuit data in order to construct a second circuit, on the basis of first circuit data so as to construct a first circuit along with a change of selection of illumination light to be supplied to the object;
- a second control step of transmitting a tentative image during reconstructing, that is, until the first control step is completed; and
- a third control step of transmitting a second image, which has undergone image processing performed by the first circuit constructed using the programmable circuit unit, after the first control step is completed.

20. The image processing control method according to claim 19, wherein at the second control step, an image produced by the second circuit and stored or an image produced by causing an image signal to bypass the programmable circuit unit is transmitted.

* * * * *